United States Patent [19]

Klausener et al.

[11] Patent Number: 5,545,754
[45] Date of Patent: Aug. 13, 1996

[54] PROCESS FOR THE PREPARATION OF P-AMINO-PHENOLS

[75] Inventors: Alexander Klausener, Stolberg; Heinz Landscheidt, Duisburg; Heinz-Ulrich Blank, Odenthal-Glöbusch, all of Germany

[73] Assignee: Bayer Aktiengesellschaft, Leverkusen, Germany

[21] Appl. No.: 798,681

[22] Filed: Nov. 26, 1991

[30] Foreign Application Priority Data

Dec. 13, 1990 [DE] Germany ............... 40 39 862.5

[51] Int. Cl.⁶ .................................................. C07C 209/22
[52] U.S. Cl. ................ 564/418; 564/417; 564/423; 564/428
[58] Field of Search ................................. 564/417, 418

[56] References Cited

U.S. PATENT DOCUMENTS

| | | | |
|---|---|---|---|
| 3,637,820 | 1/1972 | Dodman et al. | 260/508 |
| 4,307,249 | 12/1981 | Derrenbacker | 564/418 |
| 4,625,062 | 11/1986 | Nagata et al. | 564/416 |
| 4,885,389 | 12/1989 | Lee et al. | 564/418 |

FOREIGN PATENT DOCUMENTS

| | | |
|---|---|---|
| 0085890 | 8/1983 | European Pat. Off. . |
| 2555575 | 5/1985 | France . |
| 2118334 | 10/1971 | Germany . |
| 1343888 | 7/1971 | Russian Federation . |

OTHER PUBLICATIONS

173752k: M. Enomoto et al., "Preparation of 4–amino–3–fluorophenol", Chem. Abstr., V. 111, No. 19 (Nov. 1989), p. 688.

55156m: Tanaka et al, "Ring–Substituted p–Aminophenols", Chem. Abstr., V. 86, No. 9 (Feb. 1977), p. 411.

Primary Examiner—Brian Burn
Attorney, Agent, or Firm—Sprung Horn Kramer & Woods

[57] ABSTRACT p-Amino-phenols are advantageously prepared by catalytic hydrogenation of the aromatic nitro compounds on which they are based in a reaction medium of aqueous sulphuric acid in the sense of a Bamberger rearrangement at elevated temperature by a procedure in which the reaction medium additionally contains a water-miscible organic solvent.

1 Claim, No Drawings

PROCESS FOR THE PREPARATION OF P-AMINO-PHENOLS

BACKGROUND OF THE INVENTION

1. Field of the Invention

The present invention relates to a process for the preparation of p-amino-phenols by catalytic hydrogenation of the aromatic nitro compounds on which they are based in a reaction medium of aqueous sulphuric acid in the sense of a Bamberger rearrangement, the reaction additionally being carried out in the presence of a water-miscible organic solvent (cosolvent).

p-Amino-phenols are of importance as intermediate products for the preparation of dyestuffs, pharmaceutical active compounds and plant protection agents.

2. Description of the Related Art

The preparation of p-amino-phenols by hydrogenation of nitroaromatics having a free p-position in an aqueous acid medium using hydrogenation catalysts is known as the Bamberger reaction in various variants (Houben-Weyl, 4th Edition, Volume VI/lc (1976), pages 85 to 117). Aqueous sulphuric acid is in general chosen as the reaction medium for the process. The rate of reaction in this process substantially depends on the solubility of the organic nitro compounds employed as the starting materials in the reaction medium or their wettability by the aqueous system. However, since this solubility or wettability of the nitroaromatics usually used as starting materials is exceptionally low, this matter represents a critical point which makes the usability of the Bamberger reaction more difficult and limits and in some cases completely prevents it.

For the reasons mentioned, in the past there has been no lack of attempts to improve the wetting of the organic nitro compound and in this way to exert a favorable influence on the course of Bamberger reactions. Thus, for example, U.S. Pat. No. 3,383,416 describes the addition of dodecylethylammoniumchloride and U.S. Pat. No. 4,307,249 describes the addition of dimethyl-alkylamine oxides as surface-active substances. According to U.S. Pat. No. 3,535,382, the addition of polyethers based on phenol of the type

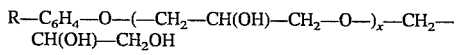

is said to be of advantage. DE-AS (German Published Specification) 1,904,574 describes a process in which the nitrobenzene used as the starting material is pumped into the reaction mixture in the course of the reaction in order to avoid a decrease in the catalytic activity of the catalyst by (as yet) unreacted, virtually water-insoluble nitrobenzene.

Disadvantages of the process variants according to the US patents mentioned are the problems associated with the auxiliaries, since these auxiliaries make isolation and purification of the desired reaction product after the reaction has ended more difficult, in general cannot be reused, magnify the waste problem and therefore impair the profitability. In the process described in the DE-AS (German Published Specification) mentioned, expensive control of the metering device is additionally necessary. Another serious disadvantage of all the abovementioned processes is that, under the conditions described, only the reaction of nitrobenzene itself and a few other nitroaromatics which still have a relatively good water-solubility and in general contain not more than one other substituent leads to satisfactory selectivities and space-time yields, but that more highly substituted nitroaromatics can be reacted only poorly and incompletely.

JP 51/110,528 (1976) describes Bamberger reactions with the addition of water-immiscible solvents, such as toluene, dibutyl ether, 1,1,1-trichloro-ethane or octanol. However, these do not improve in principle the problem of the poor wettability of the organic nitro compound by the aqueous-acid phase.

Another difficulty which often occurs in reactions of the Bamberger type is the fact that in addition to the optionally substituted p-amino-phenol required, significant amounts of the optionally substituted aminoaromatic are formed. The occurrence of this byproduct, which can assume considerable proportions which reduce profitable utilisation of the process in certain cases, is in general to be attributed to a reduction which competes with the Bamberger reaction, such as usually proceeds during the action of hydrogen on nitro compounds in the presence of noble metal catalysts. In order to influence the ratio of the desired aminophenol to the undesirable aminoaromatics advantageously, certain substances, such as, for example, dimethyl sulphoxide, are added to the reaction mixture, these partly poisoning the catalyst and moderating or reducing its catalytic activity and thus leading to a reduced formation of aminoaromatics.

A problem with this procedure is the fact that an additive is introduced into the reaction, the removal of which in the course of working up often presents problems. Furthermore, catalysts deactivated in this way cannot be re-used, which is an additional disadvantage. An example of this procedure is JP 01/121,254; cited in C. A. 111, 173 752.

The object was therefore to discover a process for the preparation of the optionally substituted 4-amino-phenols mentioned below, which on the one hand allows good wetting of the starting material in the course of the Bamberger reaction and thus leads to reaction times and yields which are of economic interest, avoids or at least largely suppresses the formation of undesirable byproducts and is carried out without the use of catalyst poisons, so that working up problems are avoided and it is ensured that the catalyst is reusable.

This object is achieved by the process according to the invention.

In contrast to the procedures described above, the process according to the invention is characterized in that it improves the use of the Bamberger reaction for the preparation of the optionally substituted 4-aminophenols mentioned below from the corresponding nitroaromatics and dispenses with the addition of catalyst poisons, so that the catalyst separated off when the reaction has ended can be reused again in the process according to the invention.

The process according to the invention is characterized in that a water-miscible organic solvent (cosolvent) is added to the reaction mixture. Such cosolvents improve the mixing of the organic and inorganic phase quite considerably, in this way have an accelerating effect on the course of the reaction and can easily be recovered when the reaction has ended, and if appropriate reused.

Finally, another surprising advantage of the process according to the invention is that sometimes considerable selectivity improvements in favor of the desired substituted p-amino-phenols are observed when such cosolvents are added.

SUMMARY OF THE INVENTION

A process has been found for the preparation of p-aminophenols of the formula

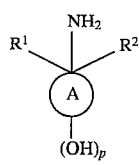

in which

A represents the benzene or naphthalene nucleus, p indicates the p-position relative to the amino group and $R^1$ and $R^2$ independently of one another denote hydrogen, $C_1$–$C_4$-alkyl, $C_1$–$C_4$-alkoxy, carboxyl, CO—$C_1$–$C_4$-alkyl or halogen, by catalytic hydrogenation of an aromatic nitro compound in an aqueous-acid reaction medium at elevated temperature, which is characterized in that, as the nitro compound, a compound of the formula

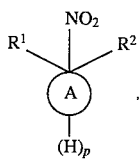

in which

A, p, $R^1$ and $R^2$ have the above meaning, is reacted in the presence of a water-miscible organic solvent.

DETAILED DESCRIPTION OF THE INVENTION

The advantageous effect produced by the addition according to the invention of the said water-miscible organic solvents (cosolvents) on the course of the Bamberger reaction in the sense of increased and rapid formation of the desired p-amino-phenol is extremely surprising. On the basis of the observations described, for example, in DE-OS (German Published Specification) 3,443,385, it would have been expected that in the presence of alcohols, for example, the corresponding p-alkoxy-aminobenzene derivatives would be formed preferably or at least to a considerable degree.

$C_1$–$C_4$-alkyl is, for example, methyl, ethyl, propyl, isopropyl, butyl or isobutyl, preferably methyl or ethyl, particularly preferably methyl.

$C_1$–$C_4$-alkoxy is, for example, methoxy, ethoxy, propoxy, isopropoxy, butoxy or isobutoxy, preferably methoxy or ethoxy, particularly preferably methoxy.

CO—$C_1$–$C_4$-alkyl (acyl) is, for example, acetyl, propionyl, butyryl, i-butyryl or butylcarbonyl.

Halogen is, for example, fluorine, chlorine or bromine, preferably fluorine or chlorine.

Preferred nitro compounds for the process according to the invention are nitrobenzenes of the formula

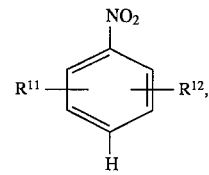

in which $R^{11}$ and $R^{12}$ independently of one another denote hydrogen, methyl, ethyl, methoxy, ethoxy, carboxyl, CO-$C_1$–$C_4$-alkyl, fluorine or chlorine.

Suitable cosolvents in the sense of the present invention are in principle all the organic water-miscible solvents which are stable under the reaction conditions used and do not adversely influence the catalytic hydrogenation. Examples of such cosolvents are lower alcohols and polyols having 1 to 4 C atoms, such as methanol, ethanol, n- and i-propanol, n-, i-, sec.- and tert-butanol, ethylene glycol, 1,2- and 1,3-propanediol, 1,2-, 1,3-, 1,4- and 2,4-butanediol and 1,2,3-propanetriol. Further examples are water-soluble ethers of the polyols mentioned, such as glycol mono- and dimethyl ether and glycol mono- and diethyl ether. Examples of other cosolvents which can be employed according to the invention are water-soluble cyclic ethers, such as tetrahydrofuran and dioxane, water-miscible ketones, such as acetone and methyl ethyl ketone, water-soluble carboxamides, in particular those which are dialkylated on the nitrogen atom, such as N,N-dimethylacetamide, N,N-dimethylformamide and the corresponding ethylated lower carboxylic acid amides, as well as lower aliphatic carboxylic acids having 1 to 4 C atoms, such as formic acid, acetic acid or propionic acid. The lower alcohols mentioned, ethylene glycol and its mono- and dimethyl ether of the type mentioned and dioxane may be mentioned as preferred. Methanol, ethanol, ethylene glycol, glycol mono- and dimethyl ether and dioxane may be mentioned as particularly preferred. The cosolvents mentioned can be employed either individually or as a mixture of several of them.

The amount of organic water-miscible solvent is 0.01 to 3 times, preferably 0.03 to 2 times, particularly preferably 0.05 to 1 times, the amount by weight of the aromatic nitro compound.

Strong inorganic or organic acids, for example sulphuric acid, phosphoric acid, nitric acid, hydrochloric acid, perchloric acid, methanesulphonic acid, toluenesulphonic acid, perfluoromethanesulphonic acid and others known to the expert, are possible for the aqueous-acid reaction medium. Sulphuric acid or one of the sulphonic acids mentioned are preferably employed; sulphuric acid is particularly preferably employed.

The amount of strong acid is 0.4–10 equivalents, preferably 0.5–2 equivalents, particularly preferably 0.5–1 equivalent, per mole of aromatic nitro compound.

The amount of water for the aqueous-acid reaction medium is 2 to 40 times, preferably 3 to 30 times, particularly preferably 4 to 20 times, the amount by weight of the aromatic nitro compound.

The process according to the invention is carried out at a temperature of 50° to 160° C., preferably 60° to 140° C., particularly preferably 70° to 120° C.

For the catalytic hydrogenation in the context of the process according to the invention, the reaction is carried out under increased pressure, for which reason it is carried out in any type of pressure reactor such as is known to the expert. Such a reactor is of course acid-resistant under the reaction conditions to be established according to the invention. A pressure of 2 bar up to 50 bar may be mentioned as the increased pressure. The hydrogen partial vapor pressure participates in this increased pressure with a proportion of 0.1 to 50 bar, preferably 0.5 to 30 bar, particularly preferably 1 to 20 bar, and can thus also make up the total pressure of up to 50 bar. The difference between the hydrogen partial vapor pressure and the total pressure is in general the autogenous pressure of the reaction system, that is to say the vapor pressure of the water and the organic water-miscible solvent to be added. The vapor pressure of the nitro compound is also involved. To ensure the smooth course of a catalytic hydrogenation, flushing with an inert gas, such as nitrogen, a noble gas or the like, is furthermore necessary after the pressure reactor has been filled with the substances to be reacted and the reaction medium. Any residue of the inert flushing gas which remains in the pressure reactor after this has been closed also contributes towards the total pressure. In this context, a procedure is in general followed in which the closed pressure reactor is brought to the desired reaction temperature before the hydrogen partial vapor pressure is established by forcing in hydrogen. Hydrogen is then subsequently added for as long as it is taken up by the reaction mixture.

Possible catalysts for the process according to the invention are noble metals of the platinum group, in particular platinum and/or palladium. Compounds of platinum metals, for example platinum compounds and/or palladium compounds, can similarly be employed. These compounds are then reduced by the hydrogenating hydrogen to give the hydrogenation-active platinum metal. The platinum metal or a compound of the platinum metal can be used with or without a support. Supports can be, for example, silica gel, aluminium oxide, zeolites, molecular sieves, charcoal or other supports which are known to the expert, preferably charcoal. If a support is used, the metal deposit is 0.05 to 8% by weight, preferably 0.1 to 6% by weight, particularly preferably 0.25 to 5% by weight of the total catalyst. The catalyst with or without a support is employed in an amount such that 0.001 to 0.3% by weight, preferably 0.005 to 0.1% by weight, particularly preferably 0.01 to 0.1% by weight of the platinum metal, based on the nitro compound to be reacted, is present.

The process according to the invention is carried out with a nitrobenzene or a 1-nitro-naphthalene, which can be substituted according to formula (II). It is preferably carried out with a nitrobenzene, which can be substituted according to formula (II).

Important aromatic nitro compounds as starting materials for the process according to the invention are: nitrobenzene, 2-nitrotoluene, 3-nitrotoluene, 2-chloronitrobenzene, 3-chloro-nitrobenzene, 2-ethylnitrobenzene, 3-ethyl-nitrobenzene, 2-acetylnitrobenzene, 3-acetyl-nitrobenzene, 2-nitrobenzoic acid and esters, 3-nitrobenzoic acid and esters, 2-fluoronitrobenzene, 3-fluoro-nitrobenzene, 2,3-dichloronitrobenzene, 2,3-difluoro-nitrobenzene, 2-chloro-3-fluoro-nitrobenzene, 2-fluoro-3-chloro-nitrobenzene and 1-nitronaphthalene.

The corresponding p-aminophenols, preferably those of the benzene series, are formed according to the invention from such nitro compounds.

The following aromatic nitro compounds of the benzene series, from which the corresponding p-aminophenols of the benzene series are formed, may be mentioned as preferred: 2,3-dichloro-nitrobenzene, 3-nitrobenzoic acid, 2-fluoro-nitrobenzene, 3-fluoronitrobenzene, 2-nitrotoluene, 3-nitrotoluene, 2-chloro-nitrobenzene, 3-chloro-nitrobenzene, 2-nitrobenzoic acid, 2-chloro-3-fluoro-nitrobenzene and 2-fluoro-3-chloro-nitrobenzene.

There may be mentioned as particularly preferred: (i) the hydrogenation according to the invention of 2,3-dichloro-nitrobenzene to give 2,3-dichloro-4-aminophenol and (ii) the hydrogenation according to the invention of 2-fluoro-nitrobenzene to give 4-amino-3-fluoro-phenol.

2,3-dichloro-4-aminophenol is an important intermediate product for the preparation of pesticides (EP 293,718).

4-Amino-3-fluoro-phenol is an important intermediate product for the preparation of insecticidal benzoyl ureas of the flufenoxuron type (EP 216,423; EP 277,748). This aminophenol is furthermore used for the preparation of various phenoxyacetic acid esters for herbicides (JP 01/125, 355; cited in C. A. 111, 232 292 k). Other fields of use of this aminophenol are herbicides of the 3,4,5,6-tetra-hydrophthalimide type (JP 53/073,557; cited in C. A. 90, 6245 p), hair coloring agents (GB 1,048,790) and antibacterial active compounds (DE-OS (German Published Specification) 3,338,846).

The preparation of 4-amino-3-fluoro-phenol can be carried out by azo coupling of diazotised sulphanilic acid to 3-fluoro-phenol and rstarting materialion of the resulting 4-(2-fluoro-4-hydroxy-phenylazo)-benzenesulphonic acid with $NaHSO_3$ (J. Chem. Soc. 1964, 473). Its preparation by Bamberger reduction of 2-fluoro-nitrobenzene has also been proposed (JP 01/121,254; cited in C. A. 111, 173,752), dimethyl sulphoxide being added to the reaction mixture.

The abovementioned disadvantages in using the processes of the prior art also apply to the preparation of 2,3-dichloro-4-aminophenol and 4-amino-3-fluoro-phenol.

The entire reaction mixture is mixed intensively during the uptake of hydrogen. For this purpose, the pressure reactor is fitted with a stirrer or with a plunger device or is constructed as a shaking autoclave.

For working up, the catalyst is separated off from the remainder of the reaction mixture by filtration, decanting or centrifugation; the remainder of the reaction mixture can then be worked up in a manner which is known in principle, for example by phase separation and subsequent distillation, crystallization or chromatography.

EXAMPLES

The liquid chromatography analyses (HPLC) were carried out as quantitative determinations by comparison with calibrated reference substances.

EXAMPLE 1

43.2 g (0.225 mol) of 2,3-dichloro-nitrobenzene, 30.0 g (0.31 mol) of sulphuric acid, 0.5 g of Pt (5 %/C), 440 ml of water and 10 ml of methanol were heated to 115° C. in a 1.3 l enamel autoclave. 10 bar of hydrogen were forced in, while stirring intensively. After 5.5 hours the reaction had ended and analysis of the reaction mixture by liquid chromatography showed the following result: 79 % of 2,3-dichloro-4-amino-phenol 21% of 2,3-dichloro-aniline.

EXAMPLE 2

28.8 g (0.15 mol) of 2,3-dichloro-nitrobenzene, 20.0 g (0.21 mol) of sulphuric acid, 0.5 g of Pt (5%/C), 300 ml of water and 50 ml of ethylene glycol were heated to 105° C.

in a 1 l glass autoclave. 2.6 bar of hydrogen were forced in, while stirring intensively. After 8 hours, the reaction had ended and analysis of the reaction mixture by liquid chromatography showed the following result: 64% of 2,3-dichloro-4-amino-phenol 36% of 2,3-dichloro-aniline.

EXAMPLE 3

96.0 g (0.5 mol) of 2,3-dichloro-nitrobenzene, 45.0 g (0.46 mol) of sulphuric acid, 0.5 g of Pt (5%/C), 400 ml of water and 50 ml of methanol were heated to 115° C. in a 1.3 l enamel autoclave. 10 bar of hydrogen were forced in, while stirring intensively. After 7 hours, the reaction had ended.

For working up, the solvents were distilled off under reduced pressure. The residue which remained was recrystallized from 300 ml of water with the addition of 2.0 g of active charcoal.

Yield: 81 g (59%) of 2,3-dichloro-4-amino-phenol hydrogen sulphate

COMPARISON EXAMPLE 1

28.8 g (0.15 mol) of 2,3-dichloro-nitrobenzene, 350 ml of water, 20 g (0.21 mol) of sulphuric acid and 1 g of Pt (5%/C) were heated to 120° C. in a 1 l glass autoclave. 3 bar of hydrogen were forced in, while stirring intensively. After 6 hours, the reaction had ended and analysis by liquid chromatography showed the following result:

35% of 2,3-dichloro-4-amino-phenol
65% of 2,3-dichloro-aniline.

EXAMPLE 4

33.4 g (0.20 mol) of 3-nitro-benzoic acid, 440 ml of water, 30 ml of methanol, 34.0 g (0.347 mol) of sulphuric acid and 1.5 g of Pt (5%/C) were heated to 120° C. in a 1.3 l enamel autoclave. 3 bar of hydrogen were forced in, while stirring intensively. After 75 minutes, the reaction had ended and analysis by liquid chromatography showed the following result:

71% of 5-amino-salicylic acid
29% of 3-amino-benzoic acid.

COMPARISON EXAMPLE 2

33.4 g (0.20 mol) of 3-nitro-benzoic acid, 470 ml of water, 34.0 g (0.347 mol) of sulphuric acid and 1.5 g of Pt (5%/C) were heated to 120° C. in a 1.3 l enamel autoclave. 3 bar of hydrogen were forced in, while stirring intensively. After 90 minutes, the reaction had ended and analysis by liquid chromatography showed the following result:

66% of 5-amino-salicylic acid and
22% of 3-amino-benzoic acid (the remainder being unidentified substances).

EXAMPLE 5

A mixture of 28.20 g (0.20 mol) of 2-fluoro-nitrobenzene, 450 ml of water, 20 ml of ethanol and 27.00 g (0.28 mol) of sulphuric acid was heated to 120° C. in a closed enamel autoclave, while stirring and with the addition of 1.50 g of Pt (5% on Norit CN1, water content 64.1%). An autogenous pressure of about 2 bar was established by this procedure. Hydrogen was forced in (partial pressure 3 bar) and hydrogenation was carried out until the uptake of $H_2$ had ended (5.5 hours). After cooling, the mixture was filtered, the residue on the filter was rinsed with a little hot water and the filtrate was extracted with 2×100 ml of ethyl acetate in order to remove residues of unreacted starting material. The aqueous phase was brought to pH 9 by addition of concentrated sodium hydroxide solution (about 38.5 ml) and perforated with ethyl acetate for about 4 hours. The organic extract was concentrated and the residue which remained was dried under reduced pressure.

Yield: 21.0 g of crude product
Analysis: HPLC 78.4% of 4-amino-3-fluoro-phenol and 13.9% of 2-fluoro-aniline (the remainder being unidentified substances).

The dark-colored crude product was boiled up with boiling petroleum ether for about 1 hour. The solid was filtered off with suction and the residue on the filter was dried under reduced pressure.

Yield: 15.0 g (60% of the theoretical yield)
Analysis: HPLC 98.5% of 4-amino-3-fluoro-phenol

COMPARISON EXAMPLE 3

A mixture of 28.20 g (0.20 mol) of 2-fluoro-nitrobenzene, 470 ml of water and 27.00 g (0.28 mol) of sulphuric acid was heated to 120° C. in a closed enamel autoclave, while stirring and with the addition of 1.50 g of Pt (5%/C). An autogenous pressure of about 2 bar was established by this procedure. Hydrogen was forced in (partial pressure 3 bar) and hydrogenation was carried out until the uptake of $H_2$ had ended. After cooling, the reaction mixture was analyzed by liquid chromatography. It was found that 35% of the 2-fluoro-nitrobenzene employed had not reacted.

EXAMPLE 6

Example 5 was repeated, but only 440 ml of water were used, and instead of the ethanol 30 ml of methanol were added to the reaction mixture.

Yield: 17.9 g (57.0%); HPLC: 100% of 4-amino-3-fluorophenol.

EXAMPLE 7

Example 6 was repeated, the catalyst separated off in Example 6 being employed.

Yield: 20.2 g (64.3%); HPLC: 100% of 4-amino-3-fluorophenol.

COMPARISON EXAMPLE 4

A catalyst recovered by reworking JP 01/121,254 was employed again and Example 5 was repeated under otherwise identical conditions. It was found that the starting material had not reacted.

What is claimed is:

1. In the preparation of a p-amino-phenol of the formula

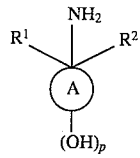

in which

A represents the benzene or naphthalene nucleus, p indicates the p-position relative to the amino group and $R^1$ and $R^2$ independently of one another denote hydrogen, $C_1$–$C_4$-alkyl, $C_1$–$C_4$-alkoxy, carboxyl, CO—$C_1$–$C_4$-alkyl or halogen, by catalytic hydrogenation in an aqueous-acid reaction medium at a temperature from 50° to 160° C. of an aromatic nitro compound of the formula

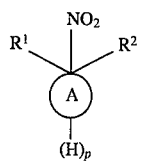

in the presence of a catalyst comprising a noble metal of the platinum group or a compound thereof the improvement which comprises effecting the hydrogenation in the presence of a water-miscible organic solvent selected from the group consisting of polyols having 1 to 4 C atoms, the mono- and dimethyl and mono- and diethyl ethers of such polyols, water-soluble cyclic ethers, water-soluble ketones, and water-soluble lower carboxylic acid amides.

* * * * *